(12) United States Patent
Arnone et al.

(10) Patent No.: US 10,183,100 B2
(45) Date of Patent: Jan. 22, 2019

(54) FLOW CONTROL SYSTEM

(71) Applicant: Kogent Surgical, LLC, Chesterfield, MO (US)

(72) Inventors: Joshua C Arnone, Wentzville, MO (US); Steven J Apperson, Ellisville, MO (US); Gregg D Scheller, Wildwood, MO (US)

( * ) Notice: Subject to any disclaimer, the term of this patent is extended or adjusted under 35 U.S.C. 154(b) by 571 days.

(21) Appl. No.: 14/513,647

(22) Filed: Oct. 14, 2014

(65) Prior Publication Data

US 2015/0148770 A1 May 28, 2015

Related U.S. Application Data

(60) Provisional application No. 61/907,460, filed on Nov. 22, 2013.

(51) Int. Cl.
*A61M 1/00* (2006.01)

(52) U.S. Cl.
CPC ........ *A61M 1/0047* (2013.01); *A61M 1/0031* (2013.01); *A61M 1/0033* (2014.02); *A61M 1/0039* (2013.01)

(58) Field of Classification Search
CPC .............. A61M 1/0047; A61M 1/0031; A61M 1/0033; A61M 1/0039; A61M 1/0064; A61M 1/0082
See application file for complete search history.

(56) References Cited

U.S. PATENT DOCUMENTS

| 5,084,045 A * | 1/1992 | Helenowski | A61B 18/1402 606/32 |
| 2004/0230169 A1* | 11/2004 | Felix | A61M 1/0047 604/317 |

OTHER PUBLICATIONS

Levy, Michael L. and McComb, J. Gordon, Integration of a Variable Action Suction Adapter in Ultrasonic Aspirators, Neurosurgery: vol. 45(4) Oct. 1999 p. 893.

* cited by examiner

*Primary Examiner* — Lauren P Farrar

(57) ABSTRACT

A flow control system may include an inner nosecone having an inner nosecone distal end and an inner nosecone proximal end, an outer nosecone having an outer nosecone distal end and an outer nosecone proximal end, an aperture of the outer nosecone, a gasket having a gasket distal end and a gasket proximal end, a gasket aperture of the gasket, a gasket seal of the gasket, a flow control mechanism having a flow control mechanism distal end and a flow control mechanism proximal end, and a control aperture of the flow control mechanism. A rotation of the flow control mechanism about the gasket may be configured to decrease an aspiration flow rate. A rotation of the flow control mechanism about the gasket may be configured to increase an aspiration flow rate.

20 Claims, 11 Drawing Sheets

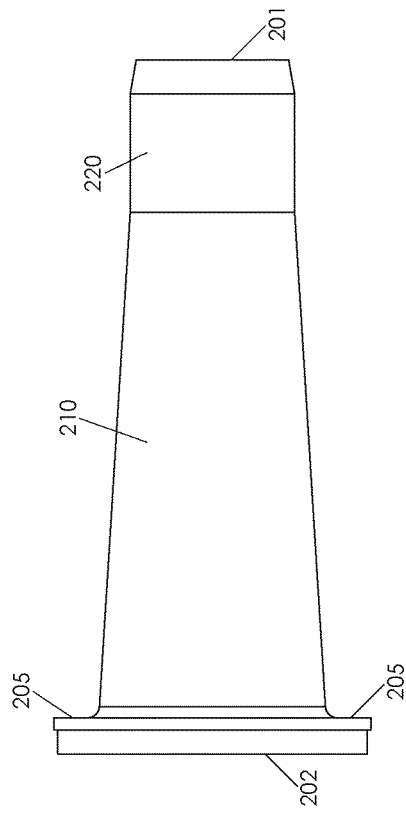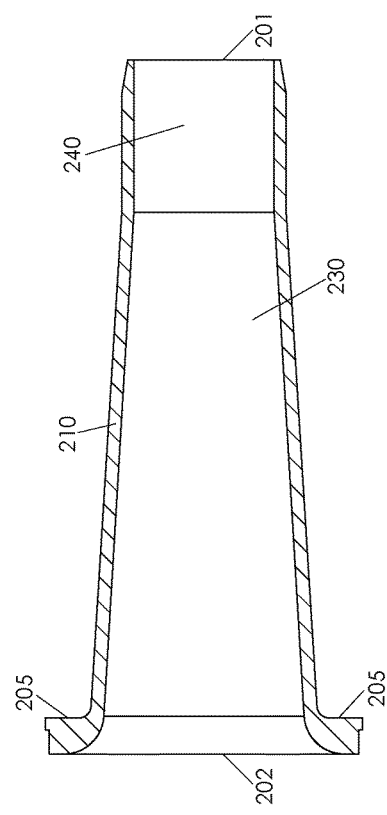

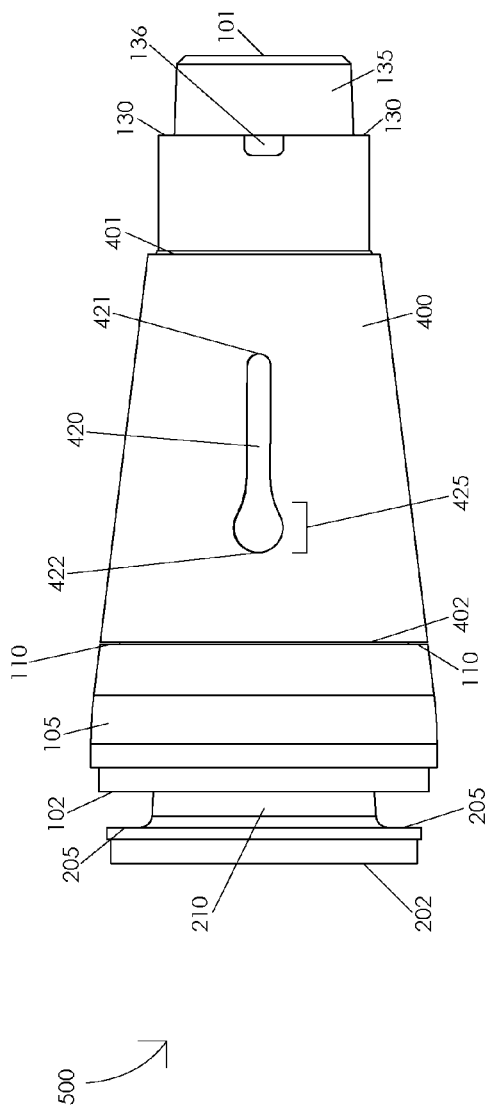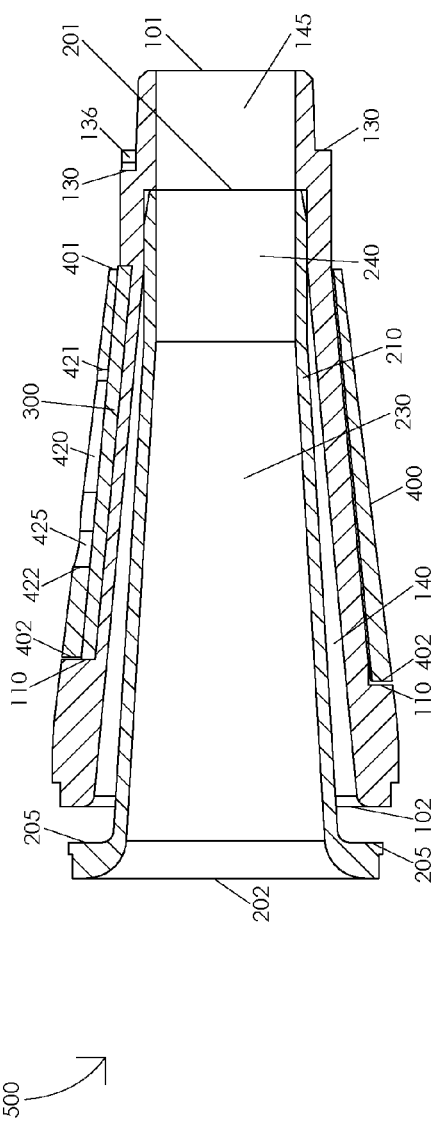
FIG. 5A
FIG. 5B

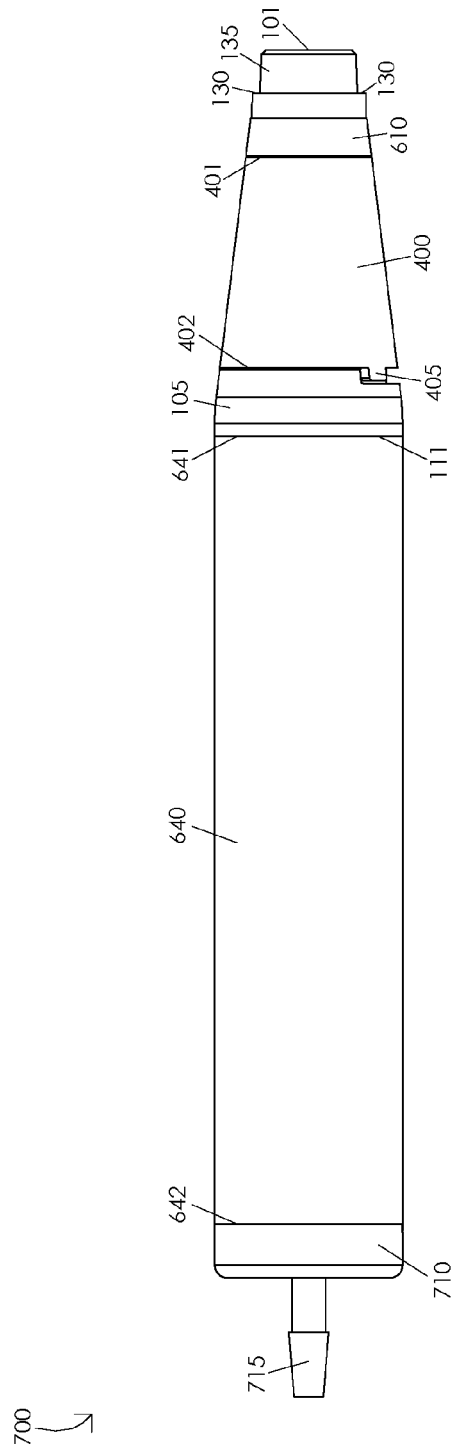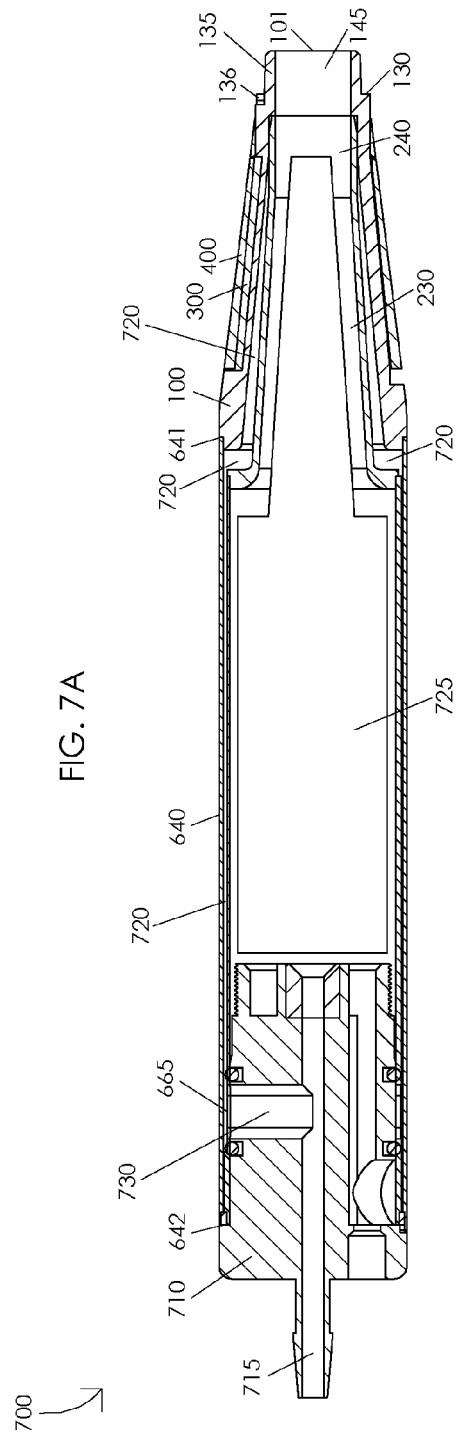
FIG. 7A
FIG. 7B

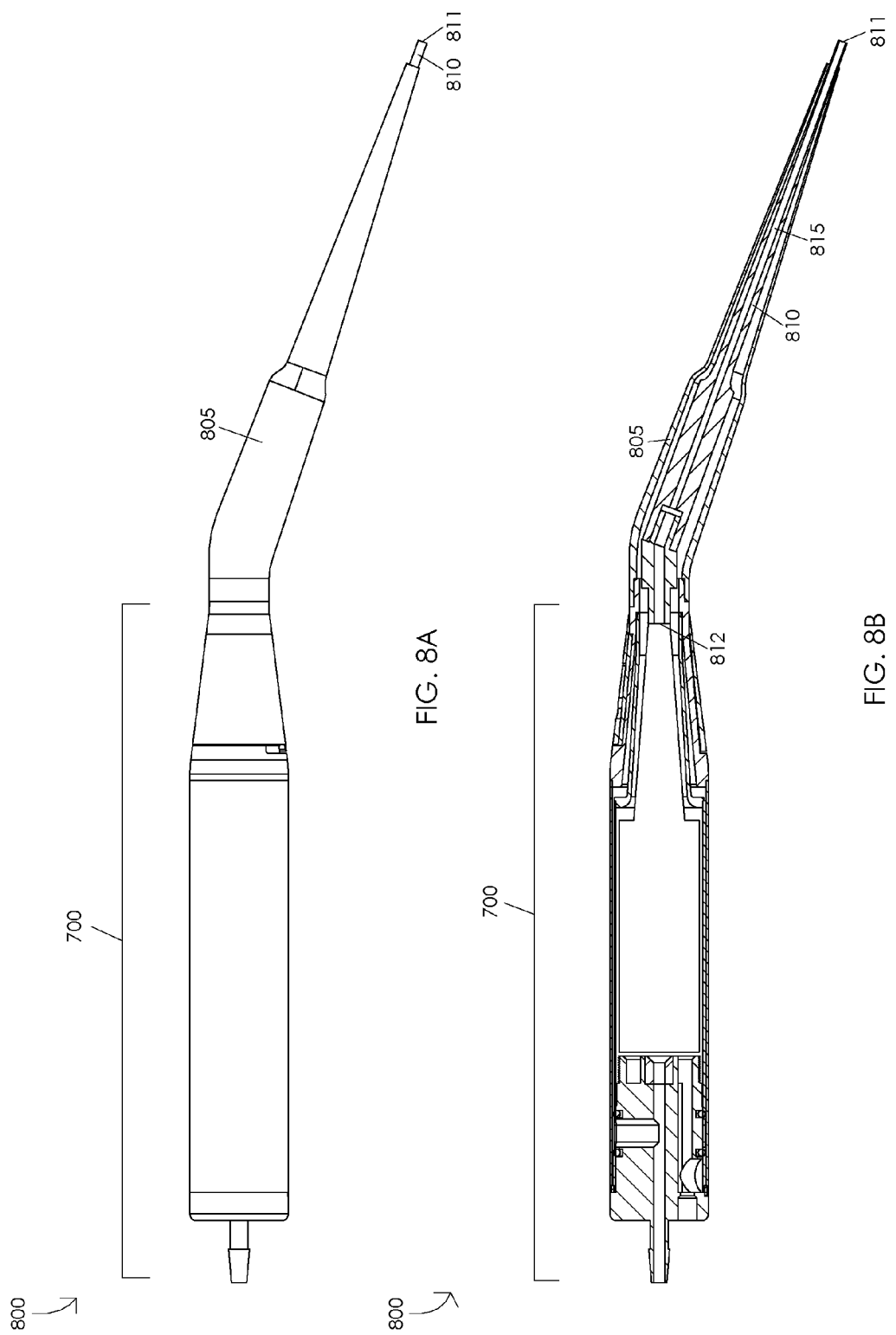

FLOW CONTROL SYSTEM

CROSS-REFERENCE TO RELATED APPLICATIONS

This Application claims the benefit of U.S. Provisional Application No. 61/907,460, filed Nov. 22, 2014.

FIELD OF THE INVENTION

The present disclosure relates to a surgical instrument for aspiration, and, more particularly, to a system for controlling an aspiration flow rate.

BACKGROUND OF THE INVENTION

A variety of surgical procedures require aspiration to remove fluid or debris from a surgical site. Typically, an aspiration handpiece is connected to a surgical machine via an aspiration tube. The surgical machine is configured to provide a vacuum pressure through the aspiration tube and the aspiration handpiece. A surgeon manipulates the handpiece to aspirate an aspiration target out from the surgical site through the handpiece and into the aspiration tube. An aspiration canister is usually disposed between the handpiece and the surgical machine for collection of fluid or debris aspirated out from the surgical site.

The surgical machine may have an adjustable aspiration flow rate, e.g., a surgical technician may adjust an aspiration flow rate by increasing or decreasing a vacuum pressure provided by the surgical machine. Increasing a vacuum pressure provided by the surgical machine may be configured to increase an aspiration flow rate and decreasing a vacuum pressure provided by the surgical machine may be configured to decrease an aspiration flow rate. A mechanism for adjusting an aspiration flow rate is typically coupled to the surgical machine, e.g., a touchscreen of the surgical machine may be configured to adjust an aspiration flow rate. This requires a surgeon to communicate a desired change in an aspiration flow rate to a surgical technician and then for the surgical technician to adjust the aspiration flow rate using a mechanism on a surgical machine.

Some surgical procedures, e.g., microsurgical procedures, require rapid changes in an aspiration flow rate in order to prevent unintended harm to a patient. For example, it may be desirable for a surgeon to immediately decrease an aspiration flow rate after aspirating an aspiration target out from a surgical site. Additionally, it may be desirable for a surgeon to immediately increase an aspiration flow rate in response to the presence of an unexpected aspiration target in a surgical site. Accordingly, there is a need for an aspiration handpiece that enables a surgeon to quickly adjust an aspiration flow rate during a surgical procedure.

BRIEF SUMMARY OF THE INVENTION

A flow control system is presented. In one or more embodiments, a flow control system may comprise an inner nosecone having an inner nosecone distal end and an inner nosecone proximal end, an outer nosecone having an outer nosecone distal end and an outer nosecone proximal end, an aperture of the outer nosecone, a gasket having a gasket distal end and a gasket proximal end, a gasket aperture of the gasket, a gasket seal of the gasket, a flow control mechanism having a flow control mechanism distal end and a flow control mechanism proximal end, and a control aperture of the flow control mechanism. Illustratively, the inner nosecone may be disposed within the outer nosecone wherein the inner nosecone proximal end extends a distance from the outer nosecone proximal end. In one or more embodiments, the gasket may be disposed over a portion of the outer nosecone wherein the gasket aperture of the gasket is disposed over the aperture of the outer nosecone. Illustratively, the flow control mechanism may be disposed over the gasket and the outer nosecone. In one or more embodiments, a rotation of the flow control mechanism about the gasket may be configured to dispose a portion of the control aperture over a portion of the gasket aperture. Illustratively, disposing a portion of the control aperture over a portion of the gasket aperture may be configured to decrease an aspiration flow rate. In one or more embodiments, a rotation of the flow control mechanism about the gasket may be configured to dispose a portion of the control aperture over a portion of the control aperture seal. Illustratively, disposing a portion of the control aperture over a portion of the control aperture seal may be configured to increase an aspiration flow rate.

BRIEF DESCRIPTION OF THE DRAWINGS

The above and further advantages of the present invention may be better understood by referring to the following description in conjunction with the accompanying drawings in which like reference numerals indicate identical or functionally similar elements:

FIGS. 2A and 2B are schematic diagrams illustrating an inner nosecone;

FIGS. 5A and 5B are schematic diagrams illustrating a flow control system;

FIGS. 7A and 7B are schematic diagrams illustrating an ultrasonic aspirator handpiece;

FIGS. 8A and 8B are schematic diagrams illustrating an assembled ultrasonic aspirator handpiece;

DETAILED DESCRIPTION OF AN ILLUSTRATIVE EMBODIMENT

Figure 1A:
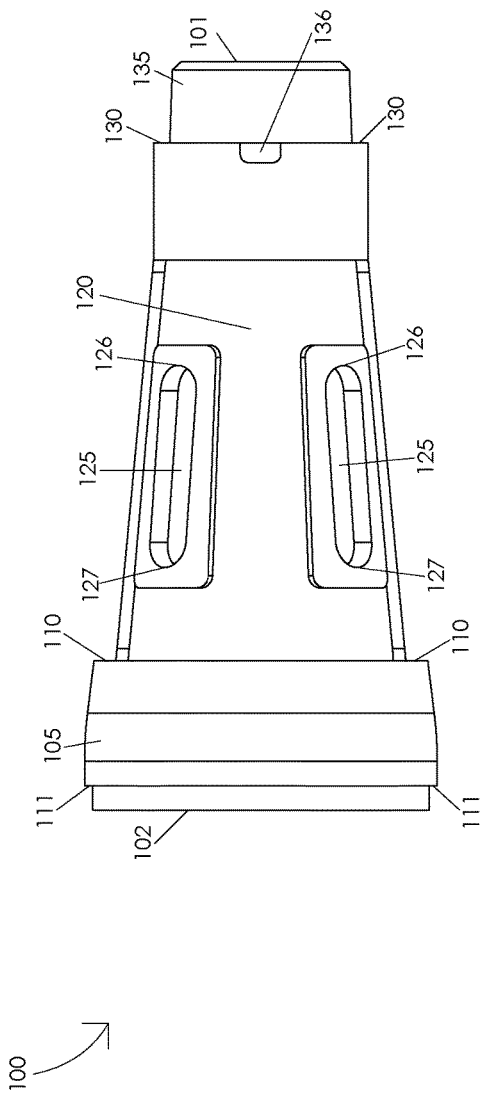
FIGS. 1A and 1B are schematic diagrams illustrating an outer nosecone.
Figure 1B:
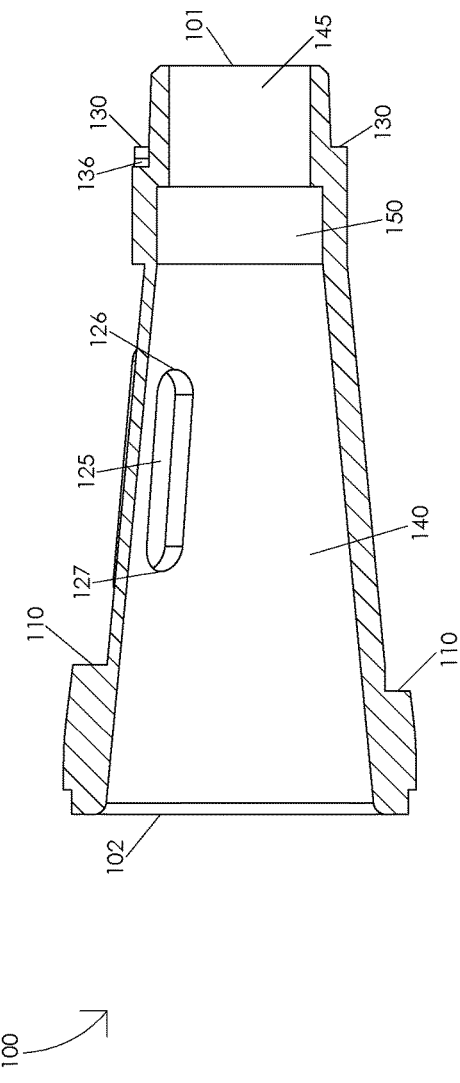

FIGS. 1A and 1B are schematic diagrams illustrating an outer nosecone 100. FIG. 1A illustrates a top view of outer nosecone 100. Illustratively, outer nosecone 100 may comprise an outer nosecone distal end 101 and an outer nosecone proximal end 102. In one or more embodiments, outer nosecone 100 may comprise a tapered flange 105 having a tapered flange distal end 110 and a tapered flange proximal end 111, a gasket interface 120, an aperture 125 having an aperture distal end 126 and an aperture proximal end 127, an irrigation sleeve flange 130, an irrigation sleeve interface 135, and an alignment tab receptacle 136. Illustratively, aperture 125 may have an aperture opening in a range of 0.05 to 0.25 square inches, e.g., aperture 125 may have an aperture opening of 0.13 square inches. In one or more embodiments, aperture 125 may have an aperture opening of less than 0.05 square inches or greater than 0.25 square inches. Illustratively, outer nosecone 100 may comprise a first aperture 125 having a first aperture distal end 126 and a first aperture proximal end 127 and a second aperture 125 having a second aperture distal end 126 and a second aperture proximal end 127. In one or more embodiments, outer nosecone 100 may be manufactured from any suitable material, e.g., polymers, metals, metal alloys, etc., or from any combination of suitable materials. FIG. 1B illustrates a cross-sectional view of outer nosecone 100. In one or more embodiments, outer nosecone 100 may comprise an inner chamber 140, an outer nosecone distal bore 145, and an inner nosecone interface 150.

FIGS. 2A and 2B are schematic diagrams illustrating an inner nosecone 200. FIG. 2A illustrates a top view of inner nosecone 200. In one or more embodiments, inner nosecone 200 may comprise an inner nosecone distal end 201, an inner nosecone proximal end 202, a flange 205, a conical body 210, and an outer nosecone interface 220. Illustratively, inner nosecone 200 may be manufactured from any suitable material, e.g., polymers, metals, metal alloys, etc., or from any combination of suitable materials. FIG. 2B illustrates a cross-sectional view of inner nosecone 200. Illustratively, inner nosecone 200 may comprise an inner nosecone proximal bore 230 and an inner nosecone distal bore 240. In one or more embodiments, a portion of inner nosecone 200 may be disposed within outer nosecone 100, e.g., inner nosecone distal end 201 may be disposed within inner nosecone interface 150. Illustratively, a portion of inner nosecone 200 may be fixed within a portion of outer nosecone 100, e.g., inner nosecone distal end 201 may be fixed within inner nosecone interface 150. In one or more embodiments, inner nosecone distal end 201 may be fixed within inner nosecone interface 150 by a friction fit, a weld, an adhesive, etc. Illustratively, a portion of inner nosecone 200 may be configured to extend out from outer nosecone 100, e.g., inner nosecone proximal end 202 may be configured to extend a distance from outer nosecone proximal end 102. In one or more embodiments, flange 205 may be configured to extend from outer nosecone proximal end 102 by a distance in a range of 0.10 to 0.25 inches, e.g., flange 205 may extend 0.17 inches from outer nosecone proximal end 102. Illustratively, flange 205 may be configured to extend a distance from outer nosecone proximal end 102 by a distance of less than 0.10 inches or greater than 0.25 inches.

Figure 3A:
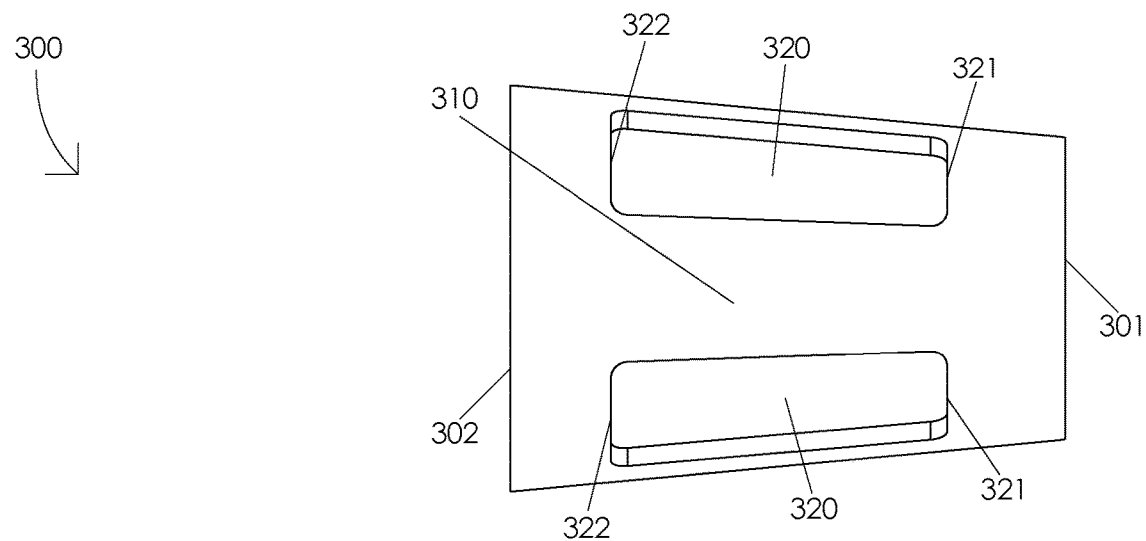
FIGS. 3A and 3B are schematic diagrams illustrating a gasket.
Figure 3B:
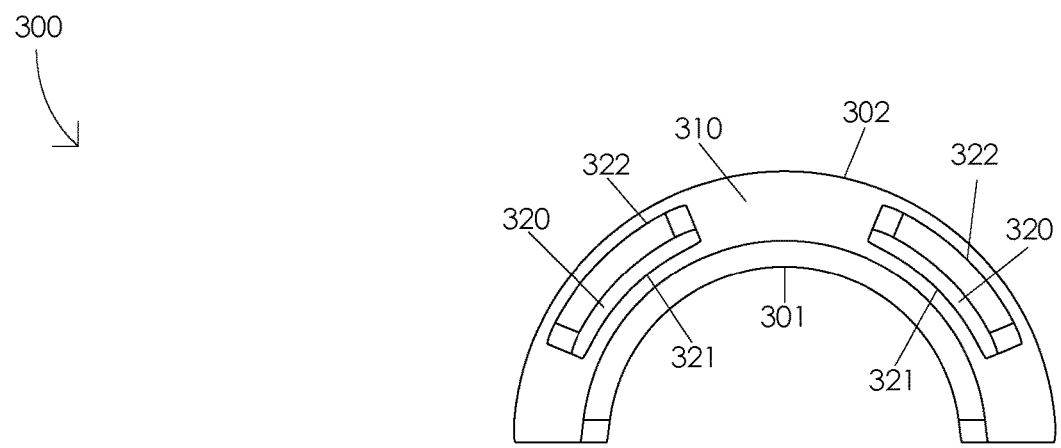

FIGS. 3A and 3B are schematic diagrams illustrating a gasket 300. FIG. 3A illustrates a top view of gasket 300. FIG. 3B illustrates a front view of gasket 300. Illustratively, gasket 300 may comprise a gasket distal end 301, a gasket proximal end 302, a control aperture seal 310, and a gasket aperture 320 having a gasket aperture distal end 321 and a gasket aperture proximal end 322. In one or more embodiments, gasket aperture 320 may have a gasket aperture opening in a range of 0.05 to 0.25 square inches, e.g., gasket aperture 320 may have a gasket aperture opening of 0.13 square inches. Illustratively, gasket aperture 320 may have a gasket aperture opening of less than 0.05 square inches or greater than 0.25 square inches. In one or more embodiments, gasket 300 may comprise a first gasket aperture 320 having a first gasket aperture distal end 321 and a first gasket aperture proximal end 322 and a second gasket aperture 320 having a second gasket aperture distal end 321 and a second gasket aperture proximal end 322. Illustratively, gasket 300 may be manufactured from any suitable material, e.g., polymers, metals, metal alloys, etc., or from any combination of suitable materials. In one or more embodiments, gasket 300 may be an elastomer, e.g., gasket may be manufactured from silicone, EPDM, etc. Illustratively, gasket 300 may have a hardness in a range of 30.0 to 70.0 Shore A durometer, e.g., gasket 300 may have a hardness of 60.0 Shore A durometer. In one or more embodiments, gasket 300 may have a hardness of less than 30.0 Shore A durometer or greater than 70.0 Shore A durometer. In one or more embodiments, gasket 300 may be manufactured from a material suitable for sterilization by a medical autoclave. Illustratively, gasket 300 may be manufactured from a material configured to withstand exposure to temperatures, pressures, and ambient conditions present in a medical autoclave without degradation. For example, gasket 300 may be configured to function normally after exposure in a temperature 250° F. for 15 minutes at an atmospheric pressure of 15 psi. In one or more embodiments, gasket 300 may be configured to be used in a surgical procedure and then sterilized by a medical autoclave at least three times. Illustratively, gasket 300 may be configured to be used in a surgical procedure and then sterilized by a medical autoclave more than three times.

Figure 4A:
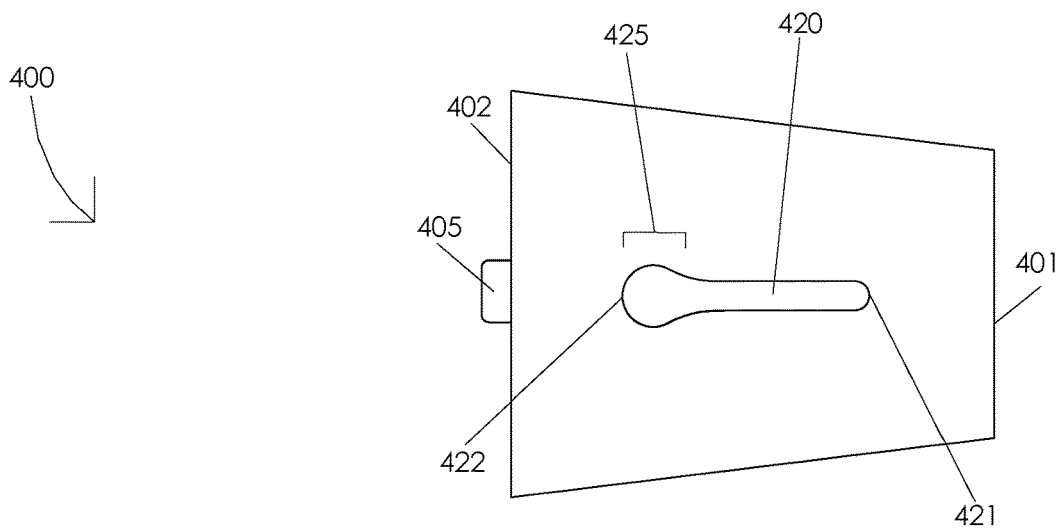
FIGS. 4A and 4B are schematic diagrams illustrating a flow control mechanism.
Figure 4B:
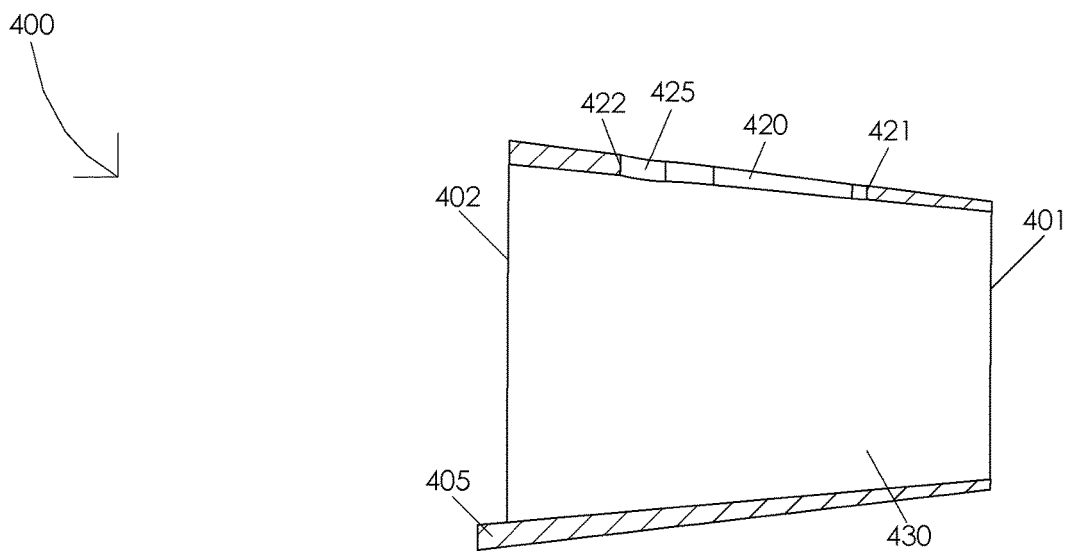

FIGS. 4A and 4B are schematic diagrams illustrating a flow control mechanism 400. FIG. 4A illustrates a top view of flow control mechanism 400. Illustratively, flow control mechanism 400 may comprise a flow control mechanism distal end 401, a flow control mechanism proximal end 402, a rotation stop 405, a control aperture 420 having a control aperture distal end 421 and a control aperture proximal end 422, and a control aperture proximal geometry 425. FIG. 4B illustrates a cross-sectional view of flow control mechanism 400. Illustratively, flow control mechanism 400 may comprise an inner bore 430. In one or more embodiments, control aperture 420 may have a control aperture length in a range of 0.4 to 0.6 inches, e.g., control aperture 420 may have a control aperture length of 0.5 inches. Illustratively, control aperture 420 may have a control aperture length of less than 0.4 inches or greater than 0.6 inches. In one or more embodiments, control aperture 420 may have a control aperture width in a range of 0.04 to 0.08 inches, e.g., control aperture 420 may have a control aperture width of 0.06 inches. Illustratively, control aperture 420 may have a control aperture width of less than 0.04 inches or greater than 0.08 inches. In one or more embodiments, control aperture 420 may have a variable width, e.g., a first portion of control aperture 420 may have a first width and a second portion of control aperture 420 may have a second width wherein the second width is greater than the first width. Illustratively, control aperture proximal geometry 425 may have a control aperture proximal geometry length in a range of 0.10 to 0.15 inches, e.g., control aperture proximal geometry 425 may have a control aperture proximal geometry length of 0.125 inches. In one or more embodiments, control aperture proximal geometry 425 may have a control aperture proximal geometry length of less than 0.10 inches or greater than 0.15 inches. Illustratively, control aperture proximal geometry 425 may have a variable width. In one or more embodiments, control aperture proximal geometry 425 may have a control aperture proximal geometry maximum width in a range of 0.10 to 0.15 inches, e.g., control aperture proximal geometry 425 may have a control aperture proximal geometry maximum width of 0.125 inches. Illustratively, control aperture proximal geometry 425 may have a control aperture proximal geometry maximum width of less than 0.10 inches or greater than 0.15 inches. In one or more embodiments, flow control mechanism 400 may be manufactured from any suitable material, e.g., polymers, metals, metal alloys, etc., or from any combination of suitable materials.

FIGS. 5A and 5B are schematic diagrams illustrating a flow control system 500. FIG. 5A illustrates a top view of flow control system 500. FIG. 5B illustrates a cross-sectional view of flow control system 500. Illustratively, flow control system 500 may be configured to adjust an aspiration flow rate during a surgical procedure. In one or more embodiments, a portion of inner nosecone 200 may be disposed within a portion of outer nosecone 100, e.g., inner nosecone distal end 201 may be disposed within inner nosecone interface 150. For example, outer nosecone interface 220 may be disposed within inner nosecone interface 150. Illustratively, a portion of inner nosecone 200 may be fixed within a portion of outer nosecone 100. In one or more embodiments, gasket 300 may be disposed over a portion of outer nosecone 100, e.g., gasket 300 may be disposed over gasket interface 120. For example, gasket 300 may be disposed over gasket interface 120 wherein gasket proximal end 302 may be adjacent to tapered flange distal end 110. Illustratively, gasket 300 may be disposed over a portion of outer nosecone 100 wherein gasket aperture 320 is disposed over aperture 125. In one or more embodiments, gasket 300 may be disposed over a portion of outer nosecone 100 wherein a first gasket aperture 320 is disposed over a first aperture 125 and a second gasket aperture 320 is disposed over a second aperture 125. Illustratively, gasket 300 may be disposed over a portion of outer nosecone 100 wherein a first gasket aperture distal end 321 is adjacent to a first aperture distal end 126 and a first gasket aperture proximal end 322 is adjacent to a first aperture proximal end 127. In one or more embodiments, gasket 300 may be disposed over a portion of outer nosecone 100 wherein a second gasket aperture distal end 321 is adjacent to a second aperture distal end 126 and a second gasket aperture proximal end 322 is adjacent to a second aperture proximal end 127. Illustratively, gasket 300 may be fixed to a portion of outer nosecone 100, e.g., by an adhesive or any suitable fixation means.

In one or more embodiments, flow control mechanism 400 may be disposed over gasket 300 and outer nosecone 100, e.g., flow control mechanism 400 may be disposed over gasket 300 and outer nosecone 100 wherein control aperture 420 is disposed over a portion of gasket 300. Illustratively, gasket 300 may comprise a hermetic seal, e.g., when flow control mechanism 400 is disposed over gasket 300. Illustratively, flow control mechanism 400 may be disposed over gasket 300 and outer nosecone 100, e.g., flow control mechanism proximal end 402 may be adjacent to tapered flange distal end 110. In one or more embodiments, flow control mechanism 400 may be configured to actuate relative to outer nosecone 100, inner nosecone 200, and gasket 300, e.g., flow control mechanism 400 may be configured to rotate about outer nosecone 100, inner nosecone 200, and gasket 300. Illustratively, an application of a force to a portion of flow control mechanism 400 may be configured to rotate flow control mechanism 400 about gasket 300. In one or more embodiments, a surgeon may rotate flow control mechanism 400 by applying a force to a portion of flow control mechanism 400, e.g., a surgeon may rotate flow control mechanism 400 with a single hand. Illustratively, rotation stop 405 may be configured to limit a range of rotation of flow control mechanism 400, e.g., rotation stop 405 may be configured to prevent flow control mechanism 400 from rotating more than a maximum rotation angle. In one or more embodiments, the maximum rotation angle may comprise an angle in a range of 90.0 to 120.0 degrees, e.g., the maximum rotation angle may comprise a 100.0 degree angle.

Illustratively, a rotation of flow control mechanism 400 about gasket 300 may be configured to actuate control aperture 420 relative to gasket aperture 320. In one or more embodiments, a rotation of flow control mechanism 400 may be configured to actuate a portion of control aperture 420 over a portion of gasket aperture 320, e.g., a rotation of flow control mechanism 400 may be configured to dispose a portion of control aperture 420 over a portion of gasket aperture 320. Illustratively, a rotation of flow control mechanism 400 may be configured to increase an amount of control aperture 420 disposed over gasket aperture 320. For example, control aperture 420 may be positioned relative to gasket aperture 320 wherein a first amount of control aperture 420 is disposed over gasket aperture 320. Illustratively, a rotation of flow control mechanism 400 may be configured to position control aperture 420 wherein a second amount of control aperture 420 is disposed over gasket aperture 320. In one or more embodiments, the second amount of control aperture 420 may be greater than the first amount of control aperture 420. Illustratively, a rotation of flow control mechanism 400 may be configured to completely dispose control aperture 420 over gasket aperture 320. In one or more embodiments, rotation stop 405 may be configured to prevent additional rotation of flow control mechanism 400 after control aperture 420 is completely disposed over gasket aperture 320.

In one or more embodiments, a rotation of flow control mechanism 400 about gasket 300 may be configured to actuate control aperture 420 relative to control aperture seal 310. Illustratively, a rotation of flow control mechanism 400 about gasket 300 may be configured to dispose a portion of control aperture 420 over a portion of control aperture seal 310. In one or more embodiments, a rotation of flow control mechanism 400 about gasket 300 may be configured to increase an amount of control aperture 420 disposed over control aperture seal 310. Illustratively, a rotation of flow control mechanism 400 about gasket 300 may be configured to completely dispose control aperture 420 over control aperture seal 310. In one or more embodiments, control aperture seal 310 may be configured to hermetically seal control aperture 420, e.g., when control aperture 420 is completely disposed over control aperture seal 310. Illustratively, when control aperture 420 is completely disposed over control aperture seal 310, a rotation of flow control mechanism 400 in a first direction may be configured to dispose a portion of control aperture 420 over a portion of a first gasket aperture 320 and a portion of a first aperture 125. In one or more embodiments, when control aperture 420 is completely disposed over control aperture seal 310, a rotation of flow control mechanism 400 in a second direction may be configured to dispose a portion of control aperture 420 over a portion of a second gasket aperture 320 and a portion of a second aperture 125.

Figure 6:
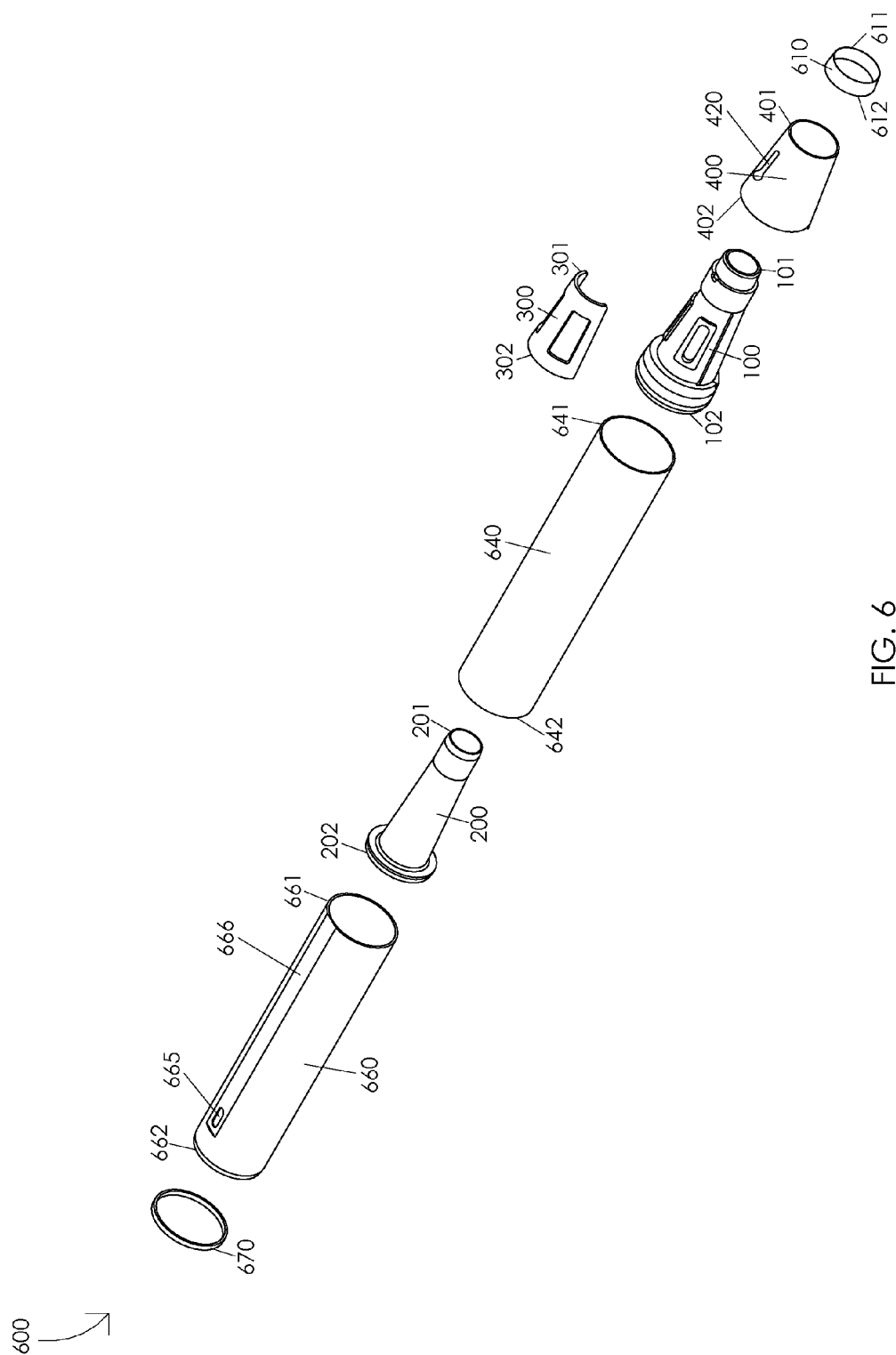
FIG. 6 is a schematic diagram illustrating an exploded view of a housing assembly.

FIG. 6 is a schematic diagram illustrating an exploded view of a housing assembly 600. In one or more embodiments, housing assembly 600 may comprise a retaining ring 610 having a retaining ring distal end 611 and a retaining ring proximal end 612, a flow control mechanism 400 having a flow control mechanism distal end 401 and a flow control mechanism proximal end 402, a gasket 300 having a gasket distal end 301 and a gasket proximal end 302, an outer nosecone 100 having an outer nosecone distal end 101 and an outer nosecone proximal end 102, an outer housing tube 640 having an outer housing tube distal end 641 and an outer housing tube proximal end 642, an inner nosecone 200 having an inner nosecone distal end 201 and an inner nosecone proximal end 202, an inner housing tube 660 having an inner housing tube distal end 661 and an inner housing tube proximal end 662, and a proximal ring 670. Illustratively, retaining ring 610, outer housing tube 640, inner housing tube 660, and proximal ring 670 may be manufactured from any suitable material, e.g., polymers, metals, metal alloys, etc., or from any combination of suitable materials. In one or more embodiments, inner housing tube 660 may comprise a flow junction interface 665 and a flow facilitation channel 666.

Illustratively, outer housing tube 640 may be disposed over a portion of flow control system 500, e.g., outer housing tube 640 may be disposed over a portion of outer nosecone 100. In one or more embodiments, outer housing tube 640 may be disposed over outer nosecone 100 wherein outer housing tube distal end 641 may be adjacent to tapered flange proximal end 111. Illustratively, a portion of outer housing tube 640 may be fixed to a portion of outer nosecone 100, e.g., by an adhesive or any suitable fixation means. In one or more embodiments, a portion of outer housing tube 640 may be fixed to a portion of outer nosecone 100, e.g., by a weld, by a press fit, etc. Illustratively, a portion of outer housing tube 640 fixed to a portion of outer nosecone 100 may comprise a hermetic seal. In one or more embodiments, an interface between outer housing tube 640 and outer nosecone 100 may comprise a hermetic seal, e.g., an interface between outer housing tube distal end 641 and tapered flange proximal end 111 may comprise a hermetic seal. Illustratively, outer housing tube 640 may be disposed over a portion of flow control system 500, e.g., outer housing tube 640 may be disposed over a portion of inner nosecone 200.

In one or more embodiments, retaining ring 610 may be disposed over a portion of flow control system 500, e.g., retaining ring 610 may be disposed between outer nosecone distal end 101 and outer housing tube distal end 641. Illustratively, retaining ring 610 may be disposed over a portion of flow control system 500 wherein retaining ring proximal end 612 may be adjacent to flow control mechanism distal end 401. In one or more embodiments, retaining ring 610 may be fixed to a portion of flow control system 500, e.g., retaining ring 610 may be fixed to a portion of outer nosecone 100. Illustratively, retaining ring 610 may be fixed to a portion of outer nosecone 100 by an adhesive or any suitable fixation means, e.g., retaining ring 610 may be fixed to a portion of outer nosecone 100 by a weld, a press fit, etc. In one or more embodiments, retaining ring 610 may be configured to prevent an extension of flow control mechanism 400 relative to outer nosecone 100.

In one or more embodiments, proximal ring 670 may be disposed over a portion of inner housing tube 660, e.g., proximal ring 670 may be disposed over inner housing tube proximal end 662. Illustratively, proximal ring 670 may be fixed to a portion of inner housing tube 660, e.g., by an adhesive or any suitable fixation means. In one or more embodiments, an interface between proximal ring 670 and inner housing tube 660 may comprise a hermetic seal. Illustratively, inner housing tube 660 may be disposed within outer housing tube 640, e.g., inner housing tube 660 may be disposed within outer housing tube 640 wherein a portion of inner housing tube 660 may be disposed over a portion of flow control system 500. In one or more embodiments, inner housing tube 660 may be disposed within outer housing tube 640 wherein a portion of inner housing tube 660 may be disposed over a portion of inner nosecone 200, e.g., inner housing tube 660 may be disposed within outer housing tube 640 wherein inner housing tube distal end 661 may be disposed over inner nosecone proximal end 202. Illustratively, inner housing tube 660 may be disposed within outer housing tube 640 wherein inner housing tube distal end 661 may be adjacent to a portion of flange 205. In one or more embodiments, a portion of inner housing tube 660 may be fixed to a portion of inner nosecone 200, e.g., a portion of inner housing tube 660 may be fixed to a portion of inner nosecone 200 by an adhesive, a weld, or any suitable fixation means. Illustratively, an interface between inner housing tube 660 and inner nosecone 200 may comprise a hermetic seal. In one or more embodiments, inner housing tube proximal end 662 may be disposed within outer housing tube 640, e.g., proximal ring 670 may be disposed within outer housing tube 640.

FIGS. 7A and 7B are schematic diagrams illustrating an ultrasonic aspirator handpiece 700. FIG. 7A illustrates a side view of ultrasonic aspirator handpiece 700. In one or more embodiments, ultrasonic aspirator handpiece 700 may comprise a flow control system 500, an inner housing tube 660, an outer housing tube 640, a surgical machine interface 710, and a barb 715. Illustratively, surgical machine interface 710 may be configured to interface with a surgical machine, e.g., surgical machine interface 710 may be configured to connect to an aspiration tube. In one or more embodiments, barb 715 may be configured to interface with a surgical machine, e.g., barb 715 may be configured to connect to an aspiration tube. Illustratively, a surgical machine may be configured to facilitate an aspiration vacuum within an inner portion of ultrasonic aspirator handpiece 700, e.g., a surgical machine may be configured to create an aspiration vacuum in an aspiration lumen within ultrasonic aspirator handpiece 700 to facilitate aspiration of a surgical site. In one or more embodiments, a surgical machine may be configured to create an aspiration vacuum within an aspiration lumen having a vacuum pressure in a range of 20.0 to 30.0 inHg at 27° C., e.g., a surgical machine may be configured to create an aspiration vacuum within an aspiration lumen having a vacuum pressure of 26.0 inHg at 27° C. Illustratively, a surgical machine may be configured to create an aspiration vacuum within an aspiration lumen having a vacuum pressure of less than 20.0 inHg or greater than 30.0 inHg at 27° C. For example, ultrasonic aspirator handpiece 700 may interface with a surgical machine to provide aspiration for removal of blood, bone, tissue, etc. Illustratively, ultrasonic aspirator handpiece 700 may be manufactured from any suitable material, e.g., polymers, metals, metal alloys, etc., or from any combination of suitable materials.

FIG. 7B illustrates a cross-sectional view of ultrasonic aspirator handpiece 700. In one or more embodiments, ultrasonic aspirator handpiece 700 may comprise a flow control channel 720, an ultrasonic transducer 725, and a flow junction 730. Illustratively, inner housing tube 660 may be disposed within outer housing tube 640 wherein flow facilitation channel 666 and an inner portion of outer housing tube 640 form a portion of flow control channel 720. In one or more embodiments, inner housing tube 660 may be disposed within outer housing tube 640 wherein flow junction interface 665 is disposed over flow junction 730, e.g., flow junction interface 665 may be configured to connect flow junction 730 and flow control channel 720. Illustratively, flow junction 730 may be configured to connect flow control channel 720 to an aspiration lumen within ultrasonic aspirator handpiece 700.

Illustratively, ultrasonic aspirator handpiece 700 and a surgical machine may be configured to aspirate an aspiration target out from a surgical site and into an aspiration lumen within ultrasonic aspirator handpiece 700, e.g., the surgical machine may be configured to decrease a pressure within in the aspiration lumen wherein the pressure within the aspiration lumen is lower than a pressure of the surgical site. In one or more embodiments, ultrasonic aspirator handpiece 700 and the surgical machine may be configured to aspirate the aspiration target out from the aspiration lumen within ultrasonic aspirator handpiece 700 and into an aspiration tube, e.g., the surgical machine may be configured to decrease a pressure within the aspiration tube wherein the pressure within the aspiration tube is lower than the pressure within the aspiration lumen. Illustratively, the surgical machine may be configured to aspirate the aspiration target out from the aspiration tube and into an aspiration canister, e.g., the surgical machine may be configured to decrease a pressure within the aspiration canister wherein the pressure within the aspiration canister is lower than the pressure within the aspiration tube. In one or more embodiments, the aspiration canister may be configured to collect aspirated material during a surgical procedure for disposal after the surgical procedure.

FIGS. 8A and 8B are schematic diagrams illustrating an assembled ultrasonic aspirator handpiece 800. FIG. 8A illustrates a side view of an assembled ultrasonic aspirator handpiece 800. FIG. 8B illustrates a cross-sectional view of an assembled ultrasonic aspirator handpiece 800. In one or more embodiments, assembled ultrasonic aspirator handpiece 800 may comprise an ultrasonic aspirator handpiece 700, an irrigation sleeve 805, an ultrasonic aspirator tip 810 having an ultrasonic aspirator tip distal end 811, an ultrasonic aspirator tip proximal adapter 812, and an aspiration channel 815. Illustratively, assembled ultrasonic aspirator handpiece 800 may be configured to interface with a surgical machine to aspirate an aspiration target out from a surgical site. In one or more embodiments, a surgeon may maneuver ultrasonic aspirator tip 810 to aspirate an aspiration target out from a surgical site, e.g., a surgeon may maneuver ultrasonic aspirator tip distal end 811 to aspirate the aspiration target out from a surgical site. Illustratively, assembled ultrasonic aspirator handpiece 800 may be configured to interface with a surgical machine to aspirate an aspiration target out from a surgical site and into ultrasonic aspirator tip 810, e.g., assembled ultrasonic aspirator handpiece 800 may be configured to aspirate an aspiration target out from a surgical site and into aspiration channel 815. In one or more embodiments, a surgical machine may be configured to decrease a pressure within aspiration channel 815 wherein a pressure within aspiration channel 815 is lower than a pressure of a surgical site. Illustratively, assembled ultrasonic aspirator handpiece 800 and a surgical machine may be configured to aspirate an aspiration target out from aspiration channel 815 and into an aspiration lumen within assembled ultrasonic aspirator handpiece 800, e.g., assembled ultrasonic aspirator handpiece 800 may be configured to aspirate an aspiration target out from ultrasonic aspirator tip proximal adapter 812 and into an aspiration lumen within assembled ultrasonic aspirator handpiece 800. In one or more embodiments, a surgical machine may be configured to reduce a pressure within an aspiration lumen wherein a pressure within the aspiration lumen is lower than a pressure within aspiration channel 815. Illustratively, assembled ultrasonic aspirator handpiece 800 and a surgical machine may be configured to aspirate an aspiration target out from an aspiration lumen within assembled ultrasonic aspirator handpiece 800 and into an aspiration tube, e.g. a surgical machine may be configured to decrease a pressure within an aspiration tube wherein a pressure within the aspiration tube is lower than a pressure within an aspiration lumen. In one or more embodiments, a surgical machine may be configured to aspirate an aspiration target out from an aspiration tube and into an aspiration canister, e.g., a surgical machine may be configured to decrease a pressure within an aspiration canister wherein a pressure within the aspiration canister is lower than a pressure within an aspiration tube. Illustratively, an aspiration canister may be configured to collect aspirated material during a surgical procedure for disposal after the surgical procedure.

In one or more embodiments, a surgical machine may be configured to decrease a pressure within flow control channel 720, e.g., a surgical machine may be configured to decrease a pressure within flow junction 730. Illustratively, a surgical machine may be configured to decrease a pressure within flow control channel 720 and flow junction 730 wherein a pressure within flow channel 720 is equal to a pressure within flow junction 730. In one or more embodiments, a surgical machine may be configured to decrease a pressure within flow junction 730 wherein a pressure within flow junction 730 is equal to a pressure within a portion of an aspiration lumen, e.g., an interface between flow junction 730 and an aspiration lumen may have a pressure equal to a pressure within flow junction 730. Illustratively, a surgical machine may be configured to decrease a pressure within flow control channel 720 wherein a pressure within flow control channel 720 is equal to a pressure within a portion of an aspiration lumen, e.g., an interface between flow junction 730 and an aspiration lumen may have a pressure equal to a pressure within flow control channel 720. In one or more embodiments, decreasing a pressure within flow control channel 720 may be configured to decrease a pressure within an aspiration lumen of assembled ultrasonic aspirator handpiece 800. Illustratively, increasing a pressure within flow control channel 720 may be configured to increase a pressure within an aspiration lumen of assembled ultrasonic aspirator handpiece 800.

Illustratively, disposing a portion of control aperture 420 over a portion of gasket aperture 320 may be configured to increase a pressure within flow control channel 720, e.g., disposing a portion of control aperture 420 over a portion of gasket aperture 320 may be configured to decrease a vacuum pressure within flow control channel 720. In one or more embodiments, disposing a portion of control aperture 420 over a portion of gasket aperture 320 may be configured to increase a pressure within flow junction 730, e.g., disposing a portion of control aperture 420 over a portion of gasket aperture 320 may be configured to decrease a vacuum pressure within flow junction 730. Illustratively, disposing a portion of control aperture 420 over a portion of gasket aperture 320 may be configured to increase a pressure within an aspiration lumen of assembled ultrasonic aspirator handpiece 800, e.g., disposing a portion of control aperture 420 over a portion of gasket aperture 320 may be configured to decrease a vacuum pressure within an aspiration lumen of assembled ultrasonic aspirator handpiece 800. In one or more embodiments, increasing a pressure within an aspiration lumen of assembled ultrasonic aspirator handpiece 800 may be configured to decrease an aspiration flow rate of assembled ultrasonic aspirator handpiece 800, e.g., decreasing a vacuum pressure within an aspiration lumen of assembled ultrasonic aspirator handpiece 800 may be configured to decrease an aspiration flow rate of assembled ultrasonic aspirator handpiece 800. Illustratively, disposing a portion of control aperture 420 over a portion of gasket aperture 320 may be configured to decrease an aspiration flow rate of assembled ultrasonic aspirator handpiece 800. In one or more embodiments, increasing an amount of control aperture 420 disposed over gasket aperture 320 may be configured to increase a pressure within an aspiration lumen of assembled ultrasonic aspirator handpiece 800, e.g., increasing an amount of control aperture 420 disposed over gasket aperture 320 may be configured to decrease a vacuum pressure within an aspiration lumen of assembled ultrasonic aspirator handpiece 800. Illustratively, increasing an amount of control aperture 420 disposed over gasket aperture 320 may be configured to decrease an aspiration flow rate of assembled ultrasonic aspirator handpiece 800. In one or more embodiments, decreasing an amount of control aperture 420 disposed over gasket aperture 320 may be configured to decrease a pressure within an aspiration lumen of assembled ultrasonic aspirator handpiece 800, e.g., decreasing an amount of control aperture 420 disposed over gasket aperture 320 may be configured to increase a vacuum pressure within an aspiration lumen of assembled ultrasonic aspirator handpiece 800. Illustratively, increasing a vacuum pressure within an aspiration lumen of assembled ultrasonic aspirator handpiece 800 may be configured to increase an aspiration flow rate of assembled ultrasonic aspirator handpiece 800. In one or more embodiments, decreasing an amount of control aperture 420 disposed over gasket aperture 320 may be configured to increase an aspiration flow rate of assembled ultrasonic aspirator handpiece 800.

Figure 9A:
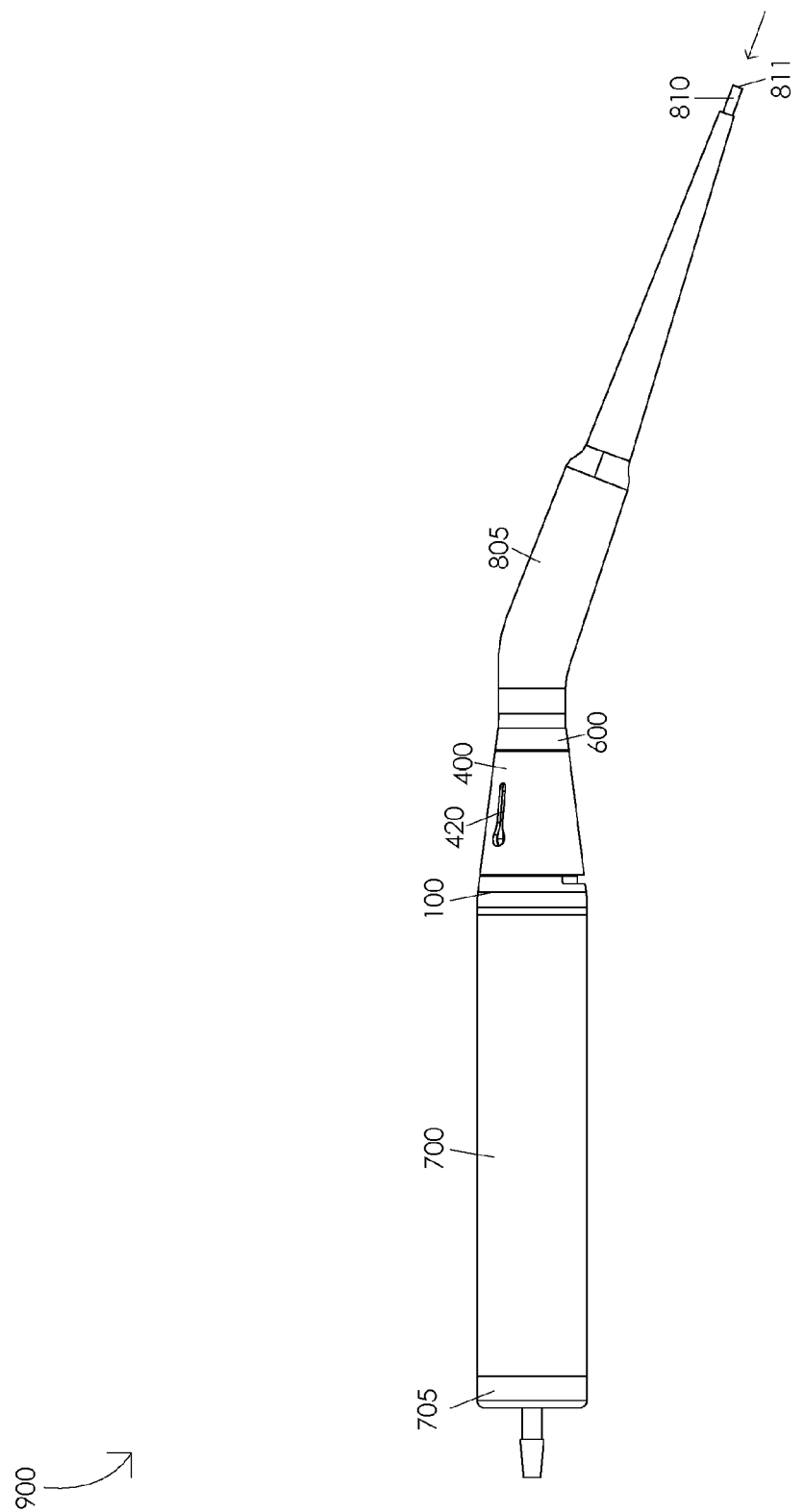
FIGS. 9A, 9B, and 9C are schematic diagrams illustrating a control of an aspiration flow rate.
Figure 9B:
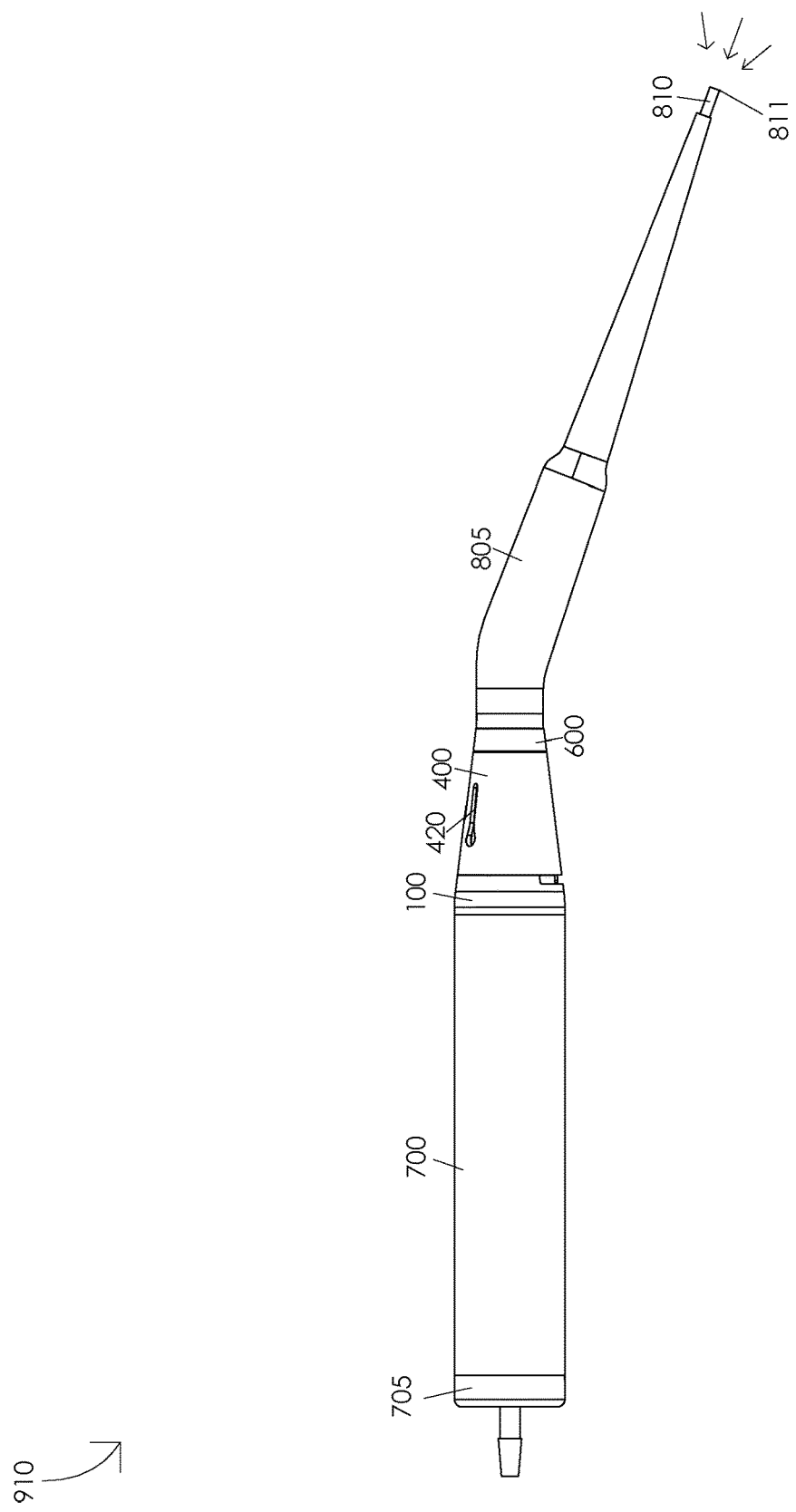
Figure 9C:
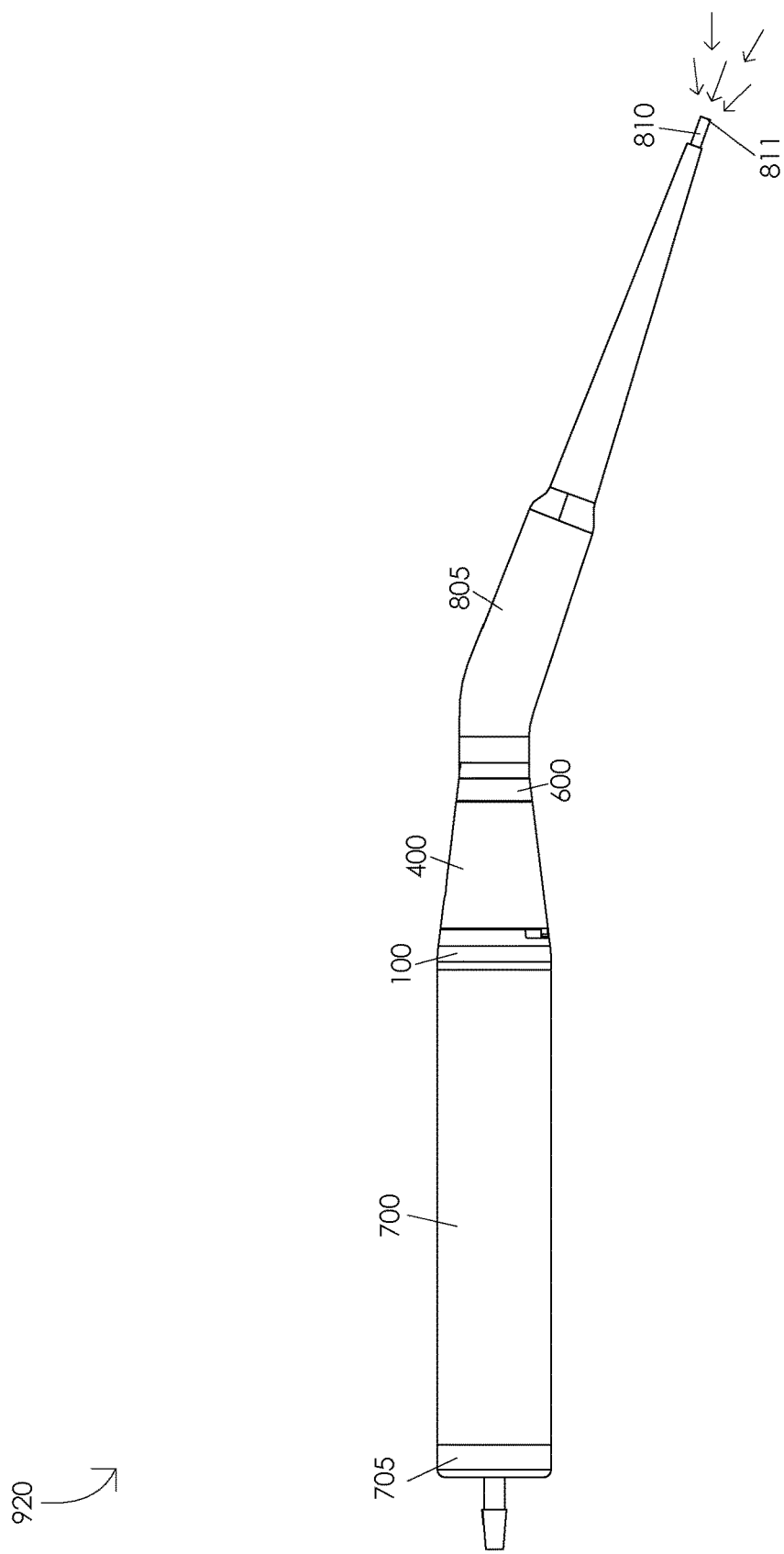

FIGS. 9A, 9B, and 9C are schematic diagrams illustrating a control of an aspiration flow rate. FIG. 9A illustrates a reduced aspiration flow rate 900. Illustratively, an aspiration flow rate of assembled ultrasonic aspirator handpiece 800 may comprise a reduced aspiration flow rate 900 when control aperture 420 is fully disposed over gasket aperture 320. In one or more embodiments, a surgeon may dispose control aperture 420 over a portion of gasket aperture 320 by rotating flow control mechanism 400 about gasket 300. Illustratively, a surgeon may dispose control aperture 420 over a portion of a first gasket aperture 320 by rotating flow control mechanism 400 about gasket 300 in a first direction. In one or more embodiments, a surgeon may dispose control aperture 420 over a portion of a second gasket aperture 320 by rotating flow control mechanism 400 about gasket 300 in a second direction. Illustratively, a surgeon may fully dispose control aperture 420 over a first gasket aperture 320 by rotating flow control mechanism 400 about gasket 300 in a first direction, e.g., until rotation stop 405 prevents further rotation of flow control mechanism 400 in the first direction. In one or more embodiments, a surgeon may fully dispose control aperture 420 over a second gasket aperture 320 by rotating flow control mechanism 400 about gasket 300 in a second direction, e.g., until rotation stop 405 prevents further rotation of flow control mechanism 400 in the second direction. Illustratively, flow facilitation channel 666 may be configured to facilitate a reduced aspiration flow rate 900, e.g., flow facilitation channel 666 may be configured to facilitate air flow within flow control channel 720 when a portion of control aperture 420 is disposed over a portion of gasket aperture 320.

FIG. 9B illustrates a partially reduced aspiration flow rate 910. Illustratively, an aspiration flow rate of assembled ultrasonic aspirator handpiece 800 may comprise a partially reduced aspiration flow rate 910 when control aperture 420 is partially disposed over gasket aperture 320. In one or more embodiments, a surgeon may dispose control aperture 420 over a portion of gasket aperture 320 by rotating flow control mechanism 400 about gasket 300. Illustratively, a surgeon may dispose control aperture 420 over a portion of a first gasket aperture 320 by rotating flow control mechanism 400 about gasket 300 in a first direction. In one or more embodiments, a surgeon may dispose control aperture 420 over a portion of a second gasket aperture 320 by rotating flow control mechanism 400 about gasket 300 in a second direction. Illustratively, a surgeon may adjust an aspiration flow rate of assembled ultrasonic aspirator handpiece 800 from a reduced aspiration flow rate 900 to a partially reduced aspiration flow rate 910, e.g., by rotating flow control mechanism 400 about gasket 300. In one or more embodiments, adjusting an aspiration flow rate of assembled ultrasonic aspirator handpiece 800 from a reduced aspiration flow rate 900 to a partially reduced aspiration flow rate 910 may be configured to increase an aspiration flow rate of assembled ultrasonic aspirator handpiece 800, e.g., a partially reduced aspiration flow rate 910 may be greater than a reduced aspiration flow rate 900.

In one or more embodiments, a flow volume of a partially reduced aspiration flow rate 910 may be in a range of 10.0 to 40.0 percent greater than a flow volume of a reduced aspiration flow rate 900, e.g., a flow volume of a partially reduced aspiration flow rate 910 may be 22.0 percent greater than a flow volume of a reduced aspiration flow rate 900. Illustratively, a flow volume of a partially reduced aspiration flow rate 910 may be less than 10.0 percent greater than a flow volume of a reduced aspiration flow rate 900. In one or more embodiments, a flow volume of a partially reduced flow rate 910 may be greater than 40.0 greater than a flow volume of a reduced aspiration flow rate 900. Illustratively, a vacuum pressure within an aspiration lumen of assembled ultrasonic aspirator handpiece 800 when a flow volume comprises a partially reduced flow volume 910 may be in a range of 10.0 to 40.0 percent less than a vacuum pressure within an aspiration lumen of assembled ultrasonic aspirator handpiece 800 when a flow volume comprises a reduced flow volume 900. In one or more embodiments, a vacuum pressure within an aspiration lumen of assembled ultrasonic aspirator handpiece 800 when a flow volume comprises a partially reduced flow volume 910 may be 25.0 percent less than a vacuum pressure within an aspiration lumen of assembled ultrasonic aspirator handpiece 800 when a flow volume comprises a reduced flow volume 900. Illustratively, a vacuum pressure within an aspiration lumen of assembled ultrasonic aspirator handpiece 800 when a flow volume comprises a partially reduced flow volume 910 may be less than 10.0 percent less than a vacuum pressure within an aspiration lumen of assembled ultrasonic aspirator handpiece 800 when a flow volume comprises a reduced flow volume 900. In one or more embodiments, a vacuum pressure within an aspiration lumen of assembled ultrasonic aspirator handpiece 800 when a flow volume comprises a partially reduced flow volume 910 may be greater than 40.0 percent less than a vacuum pressure within an aspiration lumen of assembled ultrasonic aspirator handpiece 800 when a flow volume comprises a reduced flow volume 900.

Illustratively, a surgeon may adjust an aspiration flow rate of assembled ultrasonic aspirator handpiece 800 from a reduced aspiration flow rate 900 to a partially reduced aspiration flow rate 910, e.g., by decreasing an amount of control aperture 420 disposed over gasket aperture 320. In one or more embodiments, a surgeon may adjust an aspiration flow rate of assembled ultrasonic aspirator handpiece 800 from a reduced aspiration flow rate 900 to a partially reduced aspiration flow rate 910, e.g., by covering a portion of control aperture 420 disposed over a portion of gasket aperture 320. For example, a surgeon may cover a portion of control aperture 420 disposed over a portion of gasket aperture 320 using a portion of the surgeon's hand. Illustratively, when control aperture 420 is fully disposed over gasket aperture 320, a surgeon may adjust an aspiration flow rate of assembled ultrasonic aspirator handpiece 800 from a reduced aspiration flow rate 900 to a partially reduced aspiration flow rate 910, e.g., by covering a portion of control aperture 420.

In one or more embodiments, disposing a portion of control aperture 420 over a portion of gasket aperture 320 may be configured to decrease a temperature of ultrasonic aspirator handpiece 700. Illustratively, ultrasonic transducer 725 may increase a temperature of ultrasonic aspirator handpiece 700, e.g., kinetic energy from ultrasonic transducer 725 deformations may be converted into heat during a surgical procedure. In one or more embodiments, an increase in a temperature of ultrasonic transducer 725 may increase a temperature of ultrasonic aspirator handpiece 700, e.g., heat may be conductively transferred from ultrasonic transducer 725 to outer housing tube 640. Illustratively, disposing a portion of control aperture 420 over a portion of gasket aperture 320 may be configured to decrease a temperature of ultrasonic transducer 725, e.g., disposing a portion of control aperture 420 over a portion of gasket aperture 320 may be configured to facilitate an ingress of operating room air in flow control channel 720 wherein the operating room air may have a lower temperature than a temperature of ultrasonic transducer 725. In one or more embodiments, decreasing a temperature of ultrasonic transducer 725 may be configured to decrease a temperature of ultrasonic aspirator handpiece 700. Illustratively, disposing a portion of control aperture 420 over a portion of gasket aperture 320 may be configured to prevent ultrasonic aspirator handpiece 700 from having a temperature greater than 50.0° C.

FIG. 9C illustrates a maximum aspiration flow rate 920. Illustratively, an aspiration flow rate of assembled ultrasonic aspirator handpiece 800 may comprise a maximum aspiration flow rate 920 when control aperture 420 is fully disposed over control aperture seal 310. In one or more embodiments, a surgeon may dispose control aperture 420 over a portion of control aperture seal 310 by rotating flow control mechanism 400 about gasket 300. Illustratively, a surgeon may adjust an aspiration flow rate of assembled ultrasonic aspirator handpiece 800 from a partially reduced aspiration flow rate 910 to a maximum aspiration flow rate 920, e.g., by rotating flow control mechanism 400 about gasket 300. In one or more embodiments, adjusting an aspiration flow rate of assembled ultrasonic aspirator handpiece 800 from a partially reduced aspiration flow rate 910 to a maximum aspiration flow rate 920 may be configured to increase an aspiration flow rate of assembled ultrasonic aspirator handpiece 800, e.g., a maximum aspiration flow rate 920 may be greater than a partially reduced aspiration flow rate 910. Illustratively, a surgeon may adjust an aspiration flow rate of assembled ultrasonic aspirator handpiece 800 from a partially reduced aspiration flow rate 910 to a maximum aspiration flow rate 920, e.g., by increasing an amount of control aperture 420 disposed over control aperture seal 310 until control aperture 420 is fully disposed over control aperture seal 310. In one or more embodiments, a surgeon may adjust an aspiration flow rate of assembled ultrasonic aspirator handpiece 800 from a partially reduced aspiration flow rate 910 to a maximum aspiration flow rate, e.g., by fully covering a portion of control aperture 420 disposed over a portion of gasket aperture 320. For example, a surgeon may fully cover a portion of control aperture 420 disposed over a portion of gasket aperture 320 using a portion of the surgeon's hand. Illustratively, when control aperture 420 is fully disposed over gasket aperture 320, a surgeon may adjust an aspiration flow rate of assembled ultrasonic aspirator handpiece 800 from a reduced aspiration flow rate 900 to a maximum aspiration flow rate 920, e.g., by fully covering control aperture 420. In one or more embodiments, when control aperture 420 is partially disposed over gasket aperture 320, a surgeon may adjust an aspiration flow rate of assembled ultrasonic aspirator handpiece 800 from a partially reduced aspiration flow rate 910 to a maximum aspiration flow rate 920, e.g., by fully covering a portion of control aperture 420 disposed over gasket aperture 320.

In one or more embodiments, a flow volume of a maximum aspiration flow rate 920 may be in a range of 20.0 to 80.0 percent greater than a flow volume of a reduced aspiration flow rate 900, e.g., a flow volume of a maximum aspiration flow rate 920 may be 52.0 percent greater than a flow volume of a reduced aspiration flow rate 900. Illustratively, a flow volume of a maximum aspiration flow rate 920 may be less than 20.0 percent greater than a flow volume of a reduced aspiration flow rate 900. In one or more embodiments, a flow volume of a maximum aspiration flow rate 920 may be greater than 80.0 greater than a flow volume of a reduced aspiration flow rate 900. Illustratively, a vacuum pressure within an aspiration lumen of assembled ultrasonic aspirator handpiece 800 when a flow volume comprises a maximum aspiration flow rate 920 may be in a range of 20.0 to 80.0 percent less than a vacuum pressure within an aspiration lumen of assembled ultrasonic aspirator handpiece 800 when a flow volume comprises a reduced flow volume 900. In one or more embodiments, a vacuum pressure within an aspiration lumen of assembled ultrasonic aspirator handpiece 800 when a flow volume comprises a maximum aspiration flow rate 920 may be 55.0 percent less than a vacuum pressure within an aspiration lumen of assembled ultrasonic aspirator handpiece 800 when a flow volume comprises a reduced flow volume 900. Illustratively, a vacuum pressure within an aspiration lumen of assembled ultrasonic aspirator handpiece 800 when a flow volume comprises a maximum aspiration flow rate 920 may be less than 20.0 percent less than a vacuum pressure within an aspiration lumen of assembled ultrasonic aspirator handpiece 800 when a flow volume comprises a reduced flow volume 900. In one or more embodiments, a vacuum pressure within an aspiration lumen of assembled ultrasonic aspirator handpiece 800 when a flow volume comprises a maximum aspiration flow rate 920 may be greater than 80.0 percent less than a vacuum pressure within an aspiration lumen of assembled ultrasonic aspirator handpiece 800 when a flow volume comprises a reduced flow volume 900.

In one or more embodiments, a flow volume of a maximum aspiration flow rate 920 may be in a range of 10.0 to 40.0 percent greater than a flow volume of a partially reduced aspiration flow rate 910, e.g., a flow volume of a maximum aspiration flow rate 920 may be 32.0 percent greater than a flow volume of a partially reduced aspiration flow rate 910. Illustratively, a flow volume of a maximum aspiration flow rate 920 may be less than 10.0 percent greater than a flow volume of a partially reduced aspiration flow rate 910. In one or more embodiments, a flow volume of a maximum aspiration flow rate 920 may be greater than 40.0 greater than a flow volume of a partially reduced aspiration flow rate 910. Illustratively, a vacuum pressure within an aspiration lumen of assembled ultrasonic aspirator handpiece 800 when a flow volume comprises a maximum aspiration flow rate 920 may be in a range of 10.0 to 40.0 percent less than a vacuum pressure within an aspiration lumen of assembled ultrasonic aspirator handpiece 800 when a flow volume comprises a partially reduced aspiration flow rate 910. In one or more embodiments, a vacuum pressure within an aspiration lumen of assembled ultrasonic aspirator handpiece 800 when a flow volume comprises a maximum aspiration flow rate 920 may be 26.0 percent less than a vacuum pressure within an aspiration lumen of assembled ultrasonic aspirator handpiece 800 when a flow volume comprises a partially reduced aspiration flow rate 910. Illustratively, a vacuum pressure within an aspiration lumen of assembled ultrasonic aspirator handpiece 800 when a flow volume comprises a maximum aspiration flow rate 920 may be less than 10.0 percent less than a vacuum pressure within an aspiration lumen of assembled ultrasonic aspirator handpiece 800 when a flow volume comprises a partially reduced aspiration flow rate 910. In one or more embodiments, a vacuum pressure within an aspiration lumen of assembled ultrasonic aspirator handpiece 800 when a flow volume comprises a maximum aspiration flow rate 920 may be greater than 40.0 percent less than a vacuum pressure within an aspiration lumen of assembled ultrasonic aspirator handpiece 800 when a flow volume comprises a partially reduced aspiration flow rate 910.

The foregoing description has been directed to particular embodiments of this invention. It will be apparent; however, that other variations and modifications may be made to the described embodiments, with the attainment of some or all of their advantages. Specifically, it should be noted that the principles of the present invention may be implemented in any system. Furthermore, while this description has been written in terms of a flow control system, the teachings of the present invention are equally suitable to any systems where the functionality may be employed. Therefore, it is the object of the appended claims to cover all such variations and modifications as come within the true spirit and scope of the invention.

What is claimed is:

1. An instrument comprising:
   an outer nosecone having an outer nosecone distal end and an outer nosecone proximal end;
   a first aperture of the outer nosecone;
   an irrigation sleeve flange of the outer nosecone;
   an irrigation sleeve interface of the outer nosecone;
   an inner chamber of the outer nosecone;
   an outer nosecone distal bore of the outer nosecone;
   an inner nosecone interface of the outer nosecone wherein the inner nosecone interface is disposed between the inner chamber and the outer nosecone distal bore;
   an inner nosecone having an inner nosecone distal end and an inner nosecone proximal end, the inner nosecone disposed within the outer nosecone wherein the inner nosecone proximal end extends from the outer nosecone proximal end;
   a gasket having a gasket distal end and a gasket proximal end, the gasket disposed over a portion of the outer nosecone;
   a first gasket aperture of the gasket;
   a control aperture seal of the gasket;
   a flow control mechanism having a flow control mechanism distal end and a flow control mechanism proximal end, the flow control mechanism disposed over the gasket and the outer nosecone wherein the flow mechanism is configured to rotate about the gasket; and
   a control aperture of the flow control mechanism.

2. The instrument of claim 1 wherein a rotation of the flow control mechanism about the gasket in a first direction is configured to decrease an aspiration flow rate.

3. The instrument of claim 2 wherein the rotation of the flow control mechanism about the gasket in the first direction is configured to dispose a portion of the control aperture over a portion of the first gasket aperture.

4. The instrument of claim 3 wherein a covering of the portion of the control aperture disposed over the portion of the first gasket aperture is configured to increase the aspiration flow rate.

5. The instrument of claim 3 wherein the rotation of the flow control mechanism about the gasket in the first direction is configured to increase a pressure within a flow control channel of a handpiece.

6. The instrument of claim 5 wherein the rotation of the flow control mechanism about the gasket in the first direction is configured to increase a pressure within an aspiration channel of the handpiece.

7. The instrument of claim 3 wherein a rotation of the flow control mechanism about the gasket in a second direction is configured to increase the aspiration flow rate.

8. The instrument of claim 7 wherein the rotation of the flow control mechanism about the gasket in the second direction is configured to dispose the portion of the control aperture disposed over the portion of the first gasket aperture over a portion of the control aperture seal.

9. The instrument of claim 1 further comprising:
   a second gasket aperture of the gasket.

10. The instrument of claim 9 wherein a rotation of the flow control mechanism about the gasket in a first direction is configured to decrease an aspiration flow rate.

11. The instrument of claim 10 wherein the rotation of the flow control mechanism about the gasket in the first direction is configured to dispose a portion of the control aperture over a portion of the first gasket aperture.

12. The instrument of claim 9 wherein a rotation of the flow control mechanism about the gasket in a second direction is configured to decrease an aspiration flow rate.

13. The instrument of claim 12 wherein the rotation of the flow control mechanism about the gasket in the second direction is configured to dispose a portion of the control aperture over a portion of the second gasket aperture.

14. The instrument of claim 1 further comprising:
   a handpiece;
   a surgical machine interface of the handpiece;
   an aspiration lumen of the handpiece; and
   a flow control channel of the handpiece.

15. The instrument of claim 14 further comprising:
   an outer housing tube of the handpiece having an outer housing tube distal end and an outer housing tube proximal end, the outer housing tube distal end disposed over the outer nosecone proximal end.

16. The instrument of claim 15 further comprising:
   an inner housing tube of the handpiece having an inner housing tube distal end and an inner housing tube proximal end, the inner housing tube disposed within the outer housing tube wherein the inner housing tube distal end is disposed over the inner nosecone proximal end.

17. The instrument of claim 16 further comprising:
   a flow facilitation channel of the inner housing tube, the flow facilitation channel disposed in the flow control channel.

18. An instrument comprising:
   an outer nosecone having an outer nosecone distal end and an outer nosecone proximal end;
   a first aperture of the outer nosecone;
   an irrigation sleeve flange of the outer nosecone;
   an irrigation sleeve interface of the outer nosecone;
   an inner chamber of the outer nosecone;
   an outer nosecone distal bore of the outer nosecone;

an inner nosecone interface of the outer nosecone wherein the inner nosecone interface is disposed between the inner chamber and the outer nosecone distal bore;

an inner nosecone having an inner nosecone distal end and an inner nosecone proximal end, the inner nosecone disposed within the outer nosecone wherein the inner nosecone proximal end extends from the outer nosecone proximal end;

a gasket having a gasket distal end and a gasket proximal end, the gasket disposed over a portion of the outer nosecone;

a first gasket aperture of the gasket;

a second gasket aperture of the gasket;

a control aperture seal of the gasket;

a flow control mechanism having a flow control mechanism distal end and a flow control mechanism proximal end, the flow control mechanism disposed over the gasket and the outer nosecone wherein the flow mechanism is configured to rotate about the gasket; and a control aperture of the flow control mechanism.

19. The instrument of claim 18 further comprising:

a handpiece;

a surgical machine interface of the handpiece;

an aspiration lumen of the handpiece; and a flow control channel of the handpiece.

20. The instrument of claim 19 wherein a rotation of the flow control mechanism about the gasket in a first direction is configured to decrease an aspiration flow rate.

* * * * *